United States Patent [19]

Lubkin

[11] Patent Number: 5,041,434

[45] Date of Patent: Aug. 20, 1991

[54] DRUGS FOR TOPICAL APPLICATION OF SEX STEROIDS IN THE TREATMENT OF DRY EYE SYNDROME, AND METHODS OF PREPARATION AND APPLICATION

[76] Inventor: Virginia Lubkin, One Blackstone Pl., New York, N.Y. 10471

[21] Appl. No.: 520,077

[22] Filed: May 7, 1990

[51] Int. Cl.$^5$ .................... A61K 31/565; A61K 31/57
[52] U.S. Cl. .................... 514/182; 514/169; 514/177; 514/178; 514/912; 514/914
[58] Field of Search ................ 514/169–182, 514/912–915

[56] References Cited

U.S. PATENT DOCUMENTS

| | | | |
|---|---|---|---|
| 2,861,920 | 11/1958 | Dale et al. | 514/171 |
| 3,962,430 | 6/1976 | O'Neill | 514/178 |
| 4,082,881 | 4/1978 | Chen et al. | 424/241 |
| 4,154,820 | 5/1979 | Simoons | 514/178 |
| 4,474,751 | 10/1984 | Haslam et al. | 514/171 |
| 4,474,811 | 10/1984 | Masuda et al. | 424/317 |
| 4,478,818 | 10/1984 | Shell et al. | 514/171 |
| 4,581,226 | 4/1986 | Dillon | 514/179 |
| 4,617,299 | 10/1986 | Knepper | 514/178 |
| 4,642,305 | 2/1987 | Johansson et al. | 514/182 |
| 4,774,236 | 9/1988 | Cook et al. | 514/179 |
| 4,812,448 | 3/1989 | Knepper | 514/178 |
| 4,861,763 | 8/1989 | Cook et al. | 514/179 |
| 4,863,912 | 9/1989 | Southren et al. | 514/178 |
| 4,866,049 | 9/1989 | Maumenee et al. | 514/171 |
| 4,951,683 | 8/1990 | Davis | 128/734 |
| 4,954,490 | 9/1990 | Cook et al. | 514/179 |

FOREIGN PATENT DOCUMENTS 2484252 5/1981 France .

OTHER PUBLICATIONS

Gans et al., Am. J. Opthalm. 109(4): 474–477, Apr. 1990, Estrogen and Progesterone Receptors and Human Conjunctiva.

Kramer et al., Opthalmol. 97(3): 303–307, Mar. 1990, Cyclic Changes in Conjunctival Smears from Menstruating Females.

Lamble et al., Exp. Eye Res. 26: 599–610 (1978) Some Effects of Progestogens, Oestrogens and Androgens on the Ocular Tension of Rabbits and Owl Monkeys.

Holly et al., Surv. Ophthalm. 22(2): 69–87 (1977) Review: Tear Physiology and Dry Eyes.

*Alcon (1980), Bohigian, Gro, "Handbook of External Diseases of the Eye", pp. 74–79, Dry Eye Syndrome: Diagnosis and Therapy, p. 79 (Special Rx), **** found in file of Johansson et al., U.S. Pat. No. 4,642,305.

*Alcon Brochure, Lemp, M. A. et al., "The Diagnosis and Management of the Dry Eye", **** found in file of Johansson et al., U.S. Pat. No. 4,642,305.

Johansson et al., U.S. Pat. No. 4,642,305, Swedish Priority Document, PTC Int. Search Report.

Vaughan et al., General Opthalmology, 9th Ed. (1980), pp. 54–58, Tears, Dry Eye Syndrome: KCS Keratoconjunctivitis Sicca.

Primary Examiner—Shep K. Rose

[57] ABSTRACT

A topical drug application for the alleviation of keratoconjunctivitis sicca (dry eye syndrome) is comprised of a solution of sex steroids or their derivatives suspended or dissolved in a vehicle, and the method of preparation and application of the same. In the preferred embodiments, the sex steroid consists essentially of conjugated estrogen in a lipid vehicle or a derivative of estrogen known as 17 beta-Estradiol 3-phosphate disodium dissolved in an aqueous vehicle having a pH of between 6 and 8.

7 Claims, No Drawings

DRUGS FOR TOPICAL APPLICATION OF SEX STEROIDS IN THE TREATMENT OF DRY EYE SYNDROME, AND METHODS OF PREPARATION AND APPLICATION

TECHNICAL FIELD

This invention relates to drugs for the topical application of sex steroids in the treatment of human dry eye syndrome (keratoconjunctivitis sicca) and, more specifically, to the preparation and application of estrogen and its derivatives in lipid or aqueous vehicles for the topical treatment of the ocular surface tissues.

In the specification and claims hereinafter the term 'sex steroids' is defined to include estrogen, progesterone, testosterone, dehydroepiandrosterone and chemical variants and derivatives of the same.

BACKGROUND ART

The high incidence of keratoconjunctivitis sicca in the population of postmenopausal women is attended by symptoms ranging from mild foreign body sensation to frank pain and visual loss due to ocular surface abnormalities.

The standard treatment with artificial lubricants, which provides temporary symptomatic relief in most cases does not, however, address the cause of the dry eyes. While Fried and deRoetth have anecdotally described treatment of post menopausal females with dry eye syndrome using oral premarin therapy, the oral or parenteral administration of estrogen frequently produces vaginal bleeding, breast tenderness and other undesired effects. Further, such oral or parenteral administration implicates the entire body structure in an indeterminate effort to secure an effect in a localized area (the eye), in the absence of any data relating the level of estrogen introduced into the blood stream to the level, if any, resulting in the tear fluid. Conservative medicine would indicate the desirability of limiting the specific effect of the hormone to the recipient site if possible.

BACKGROUND OF THE INVENTION

Although many enzymes, hormones and metabolites are known to be present in human tear film, there was no data showing that estrogen was or should be present in the tear fluid of normal persons. Further, there was no data correlating the dosage of orally or parenterally administered estrogen to the level, if any, of estrogen resulting in the tear fluid. Inasmuch as no significant direct evidence of estrogenic control of lacrimal function exists in the literature, both human studies and animal model were undertaken to determine the role of estrogen metabolism, if any, in dry eye syndrome.

The first series of experiments determined that sex steroids, namely estrogen and testosterone, are present in human tear film. Testosterone and 17 beta-estradiol levels were determined for blood serum, saliva, and tears by radioimmunoassay. Estradiol levels in the lacrimal and salivary secretions were found to range between 2 to 10 picograms/milliliter. Testosterone levels were found to range between 12 and 40 picograms/milliliter. The levels of estradiol and testosterone representing the free or unbound portions of these steroids, were found to approximate about 10% of matched serum levels. Further studies demonstrated that the human conjunctiva responds to the menstrual cycle.

The animal studies undertaken established the existence in lacrimal tissue of receptors with characteristics similar to those of an estrogen receptor. Lacrimal tissue was excised from 18 New Zealand Albino rabbits. Care was taken to remove only lacrimal tissue located at the inner aspect of the temporal portion of the orbit. Lacrimal tissue was rinsed in refrigerated normal saline solution stored in dry ice for less than 24 hours. The lacrimal tissue was homogenized in a 5-fold volume of TED buffer at 4 degrees C. with a TEFLON homogenizer. The homogenate was centrifuged at 130,000 g for 60 minutes and the supernatant (defined as cytosol) was removed and used immediately. The cytosol was incubated with $10^{-8}$ to $7 \times 10^{-11}$M of tagged estradiol for 20 hours at 0 degrees Centigrade with a large excess of diethylstilbestrol. (DES). Bound estradiol was separated from free estradiol by gel filtration. There was total binding in the absence of estradiol in the absence of an excess of diethylstilbestrol. Competition experiments with a variety of steroid hormones suggested that estrogen binding was to specific high affinity sites characteristic of estrogen receptors in mammalian tissues.

It was determined that:
1) Human tears contain detectable levels of estradiol and testosterone.
2) Tamoxifen and oophorectomy induce similar morphologic changes in the lacrimal gland.
3) Tamoxifen and oophorectomy alter the glycoprotein content of ocular mucus.
4) This implicates estrogens as a modulating hormone of lacrimal gland function in mammals.
5) The human conjunctiva responds to the menstrual cycle.

Prior to an application of a drug formulated in accordance with the present invention it was necessary to establish the presence of dry eye syndrome in the test population and to follow its course under treatment. The diagnosis of dry eye syndrome was made on the basis of the following tests. Initially, microscopic evaluation of the tear film with particular attention to the marginal tear strip, viscosity and debris content of the precorneal tear film, and lid examination is performed. This is followed by staining the ocular surface with Rose Bengal, a vital dye which indicates cellular damage. Schirmer testing, tear osmolarity (a measure of the melting point of a small aliquot of tears), and the maturation index (a Papanicolaou stained sample of conjunctival epithelium) are then performed. The diagnosis of menopause was confirmed with follicular stimulating hormone and luteinizing hormone serum determinants. Dry eye postmenopausal females had mean E2 (estradiol levels) of 3.47 picograms/milliliter. Normal postmenopausal females had mean E2 (estradiol levels) of 16.05 picograms/milliliter.

DISCLOSURE OF THE INVENTION

Accordingly, it is a principal object of this invention to provide treatment by topical application of drugs comprising sex steroids and their derivatives suspended or dissolved in a suitable vehicle to the conjunctival surface to alleviate dry-eye syndrome. The illustrative vehicle comprises a lipid (oil based) suspension or an aqueous solution having a pH within the range of 4-8, preferably pH 6-8. A more particular object of the invention is to provide specific drug products applicable to these purposes, and the methods of preparation and application of the same.

Preliminary Formulation

In one preliminary example of the invention, a topical drug product comprised a sterile solution of estradiol cypionate dissolved in a lipid (oil-based) vehicle at a concentration of 0.05 milligram/milliliter was tested for its effectiveness as a therapy for postmenopausal dry-eye syndrome in a controlled, double-blind study. As a pilot project, the dose was changed after one week to 0.1 milligram/milliliter, and after two weeks to 1.0 milligram/milliliter, all performed as medication in one eye and placebo (medium) in the other.

The effectiveness of estrogen and its derivatives in treating keratoconjunctivitis sicca was confirmed by the use of an intravenous sterile solution of conjugated estrogens kept refrigerated during use. The drug remained active for 60 days when refrigerated at 4–15 degrees Centigrade.

Two drops given three times a day were indicated, but it was found that application may be more or less frequent. However, it was determined that other alternative pharmaceutical modes of administration may be used—such as a slow release mode, or any other topical method, and that the concentration may vary with individual response, as well as the treatment intervals and duration. Blood levels of the hormone used were also determined. A control bottle of just the aqueous vehicle was also made, using the estrogen preparation for one eye of the patient and the control vehicle for the other eye. A dosage of the drops four times a day for several weeks, during which time osmolarity and maturation indices were performed. No change was noted in the maturation index or osmolarity, thus the concentration was increased to 0.05 milligram/milliliter. After ten days of treatment, the control eye showed no change in the experimental parameters while the eye receiving topical estrogen showed epithelial maturation commonly seen during ovulation in premenopausal females.

Preferred Formulation

It was determined to utilize as the preferred formulation, an aqueous solution of a derivative of estrogen known as 17 beta-Estradiol (the 3-phosphate disodium salt). The drug substance is also known as 17 beta-estradiol 3-phosphate disodium and 1,3,5 (10)-estratriene-3,17 beta-diol 3-phosphate disodium. The formulation is $C_{18} H_{23} O_5 P_1 Na_2$, having a molecular weight of 396.3 (anhydrous).

Each gram of 17 beta-Estradiol (as the 3-phosphate disodium salt) contains approximately 687 milligram of 17 beta-Estradiol on an anhydrous basis. 17 beta-Estradiol (as the 3-phosphate disodium salt) is available from Research Plus, Inc., Bayonne, N.J. 07002 (catalog No.1850-5). The compound is a white crystalline powder with an ill-defined melting point and purity better than 98%. The material is to be stored in sealed vials under refrigeration when not in use.

In a preferred example, a sterile, ophthalmic solution of 17 beta-Estradiol (as 3-phosphate disodium salt) is dissolved to form a 0.1% (by volume) solution in a vehicle which may in one embodiment take the form of an artificial tear solution, manufactured and sold under the trademark "absorbotear" by Alcon, Inc. Humacoa, RI 00661. The concentration of 17 beta-Estradiol in the vehicle is increased or decreased depending on the activity of the 17 beta-Estradiol (as 3-phosphate disodium salt).

EXAMPLES

A. 17 beta-Estradiol (as the 3-phosphate disodium salt) and its water-soluble, storage-stable derivatives (beta-estradiol glucuronide, beta-estradiol hemisuccinate, beta-estadiol phosphate, beta-estradiol sulfate and their 3,17 diesters, 17 monoesters and 3 monoesters). The 17 beta-estradiol 3-phosphate disodium salt is employed in the preferred embodiment because of the enhanced solubility and stability of the particular derivative at essentially neutral pH 6–8 and the ease of sterile ophthalmic manufacture.

B. The sterile ophthalmic ointment formulated to melt at body temperature containing:

| | |
|---|---|
| 17-beta Estradiol (microcrystals) | 0.1% |
| propyl paraban USP | 0.2 |
| anhydrous liquid lanolin | 5.0 |
| mineral oil USP | 10.0 |
| white petrolatum USP | 84.7 |
| | 100.0% |

C. A sterile aqueous ophthmalmic suspension and formulated to contain:

| | |
|---|---|
| 17-beta Estradiol (microcrystals) | 0.1% |
| polysorbate 80 USP | 0.2 |
| povidone USP (K-30 type) | 1.0 |
| hydroxy ethylcellulose | 0.5 |
| sodium chloride USP | 0.5 |
| disodium edetate USP | 0.05 |
| benzalkonium chloride USP | 0.005 |
| pH adjusted to 5.0 with dil. HCl | qs |
| purified water USP | qs |
| | 100.0% w/v |

D. 17-beta Estradiol or its water soluble derivatives combined with one or more of the following active ingredients for the purpose of treating associated ophthalmologic conditions in conjunction with dry eye syndrome:

1. Anti-infectives: gentamicin sulfate, neomycin sulfate, sulfacetamide sodium, chloramphenicol
2. Anti-inflammatory: dexamethasone, dexamethasone phosphate, prednisolone, prednisolone phosphase
3. Antiviral: idoxuridine
4. Antihistamine: naphazoline HCl
5. Cycloplegic: tropicamide, atropine sulfate
6. Local anesthetics: proparacaine, lidocaine
7. Miotics: pilocarpine
8. Vasoconstrictors: phenylephrine HCl The following is a description of the manufacturing and packaging procedure for a preferred drug product of our invention. More information on the preparation and characteristics of polyestradial phosphate is set forth in the article by E. Diczfalusy entitled High Molecular Weight Enzyme Inhibitors, pages 1675–1689, Chemica Scandinavia Vol. 12 (1958) No. 8, which is incorporated herein by reference.

The method of synthesis of 17 beta-Estradiol 3-phosphate disodium is reported in Acta Chem.Scan. 12, 1675–1689 (1958) and is briefly described as follows:

17 beta-Estradiol 17-acetate (Molecular Weight=314.4, Melting Point 220-224 degrees Centigrade and optical rotation+47 degrees) is phosphorylated in the presence of concentrated ortho-phosphoric acid ($H_3 PO_4$) with heat and refluxing to yield the intermediate 17 beta-Estradiol 3-phosphate 17-acetate. The latter compound is selectively hydrolyzed in the presence of sodium bicarbonate in aqueous alcohol to yield sodium acetate and 17 beta-Estradiol 3-phosphate disodium. The desired steroid phosphate ester is recrystallized from dilute alcohol.

A complete list of components present in a preferred drug product in accordance with the present invention—including the drug substance, is as follows (in percentages by volume):

17 beta-Estradiol (as 3-phosphate disodium salt) 0.1%

The concentration in subsequent batches may be increased or decreased depending upon the activity of 17 beta-Estradiol (as 3-phosphate disodium salt).

The vehicle my be supplied as a solution sold under the trademark ADSORBOTEAR Artificial Tear (solution) by Alcon (Puerto Rico) Inc., Humancao, PI 00661. The composition of the vehicle is as follows:

| | |
|---|---|
| Povidone USP | 1.67% by volume |
| Hydroxy Ethylcellulose USP | 0.44% by volume |
| Sodium Chloride USP | 0.6% by volume |
| Dried Sodium Phosphate ($Na_2 HPO_4$) USP | 0.3% by volume |
| Disodium Edetate USP | 0.1% by volume |
| Thimerosal USP | 0.004% by volume |
| pH adjusted to 7 with dilute hydrochloric acid (HCl or sodium hydroxide (NaOH) | qs |
| Purified Water USP | qs |

The preferred drug product of our invention is manufactured and packaged as follows:

i) A calculated amount of 17 beta-Estradiol (as 3-phosphate disodium salt) on an "as is basis" is weighted accurately on a suitable balance and carefully transferred to a sufficient volume of vehicle (prepared by pooling the contents of opened dropping bottles of sterile artificial tear solution) in a suitable container.

ii) The drug product is mixed using a stirring bar and a magnetic mixer until a clear solution of 17 beta-Estradiol (as 3-phosphate disodium salt) in the vehicle is obtained. (The pH of the solution may be adjusted to pH 7 with dilute hydrochloric acid (HCl) or dilute sodium hydroxide (NaOH) if required). The drug product will be brought to final volume with additional vehicle and stirring.

iii) The drug product will be sterile filtered using a filter assembly known as sterile ACRODISC disposable 0.2 micron No. 4192 (sold under the above trademark by Gelman Sciences, Inc., Ann Arbor, MI 48106) and a suitable syringe and filled directly into previously sterilized (see iv) 7 ml No. 211632 low-density polyethylene Wheaton dropping bottles with a snap-tip dropper insert and polypropylene overcap (manufactured and sold by Wheaton Scientific, Millville, New Jersey 08332). This portion of the operation will be performed directly in front of a class 100 laminar flow unit (of the type sold by Dexon, Inc., Minneapolis, MN).

iv) Air blow Wheaton dropping bottles, inserts and caps will be placed inside low density polyethylene sterilizing bag sold as MEDI-PLUS by (name company); and the bag and contents will be sterilized in a 3M ETO sterilizer, Model No. 202BA unit for 2 hours at 60 degrees Centigrade.

Based upon the chemistry of steroid phosphate esters, clarity of aqueous solution at essentially neutral pH values should be indicative of the presence of intact steroid phosphate ester. On the other hand, turbidity, haze formation or precipitate formation will indicate the presence of hydrolyzed, insoluble, free 17 beta-Estradiol.

Very small amounts of free, water-insoluble 17 beta-Estradiol can be tolerated in our drug product as long as the homogeneity of the drug product is maintained because it is the 17 beta-Estradiol itself that is undergoing clinical study and not the phosphate ester pro-drug.

Solutions of drug product are preferably stored at controlled room temperature (15 to 30 degrees Centigrade) preferably at 22 to 24 degrees Centigrade as long as adequate physical stability (i.e., clarity of solution) is maintained. Otherwise storage under refrigeration (less than 10 degrees Centigrade) may be required.

The placebo used in controlled clinical trials is the vehicle used in the manufacture of the drug product, namely Adsorbotear artificial tear solution, the formula of which is identified above. The placebo is a non-prescription, over-the-counter drug product used to provide temporary relief of dry eye symptoms. It contains mucin-like substances (povidone and hydroxy ethylcellulose) which mimic the action of the conjunctival mucus to render the surface of the eye more wetable. The vehicle helps keep the eye moist and assures that the tear film can spread easily and evenly over the eye surface.

The preferred vehicle for 17 beta-Estradiol (as 3-phosphate disodium salt) has the following attributes:

1. a sterile, buffered isotonic solution.

2. contains mucin-like substances that tend to increase the contact time between the active drug substance (17 beta-Estradiol (as the 3-phosphate disodium salt) and the eye surface.

3. free of benzalkonium chloride, which is a cationic surfactant that is known to be incompatible in solutions with steroid sodium phosphate salts.

The following quality control procedures are employed to assure identity, strength, quality and purity of the drug product:

Representative samples of finished drug product are opened and examined for clarity of solution (clear, colorless to pale yellow solution, essentially free of foreign matter), pH content (not less than 7 and not more than 8) and potency (absorbance read at 280 nanometers using 1 centimeter cells in a suitable spectrophotometer after diluting the drug product with alcohol or methanol to a suitable concentration. Comparison will be made to the absorbance of a standard solution of 17 beta-Estradiol (as 3-phosphate disodium salt)).

The quality control procedures are also the same as for the active drug product described hereinbefore with the exception that the ultraviolet absorbance at 280 nanometers of the placebo solution when diluted to the same concentration as the active drug product will fail to indicate the presence of 17 beta-Estradiol (as the 3-phosphate disodium salt) in representative samples of the placebo solution.

Although the present invention has been described with reference to several illustrative examples, it will be understood that the invention is not limited to the examples given herein by way of illustration, but only by the scope of the appended claims.

What is claimed is:

1. The method of treating Dry Eye Syndrome in postmenopausal or oophorectomized females which comprises topically applying to the lacrimal tissue to alleviate Dry Eye Syndrome in said females the drug comprising a water soluble ester of 17 Beta-Estradiol or its derivatives having a concentration of at least 0.1% weight percent dissolved or suspended in a vehicle.

2. The method in accordance with claim 1 wherein said ester is dissolved or suspended in a lipid vehicle.

3. The method in accordance with claim 1 wherein the vehicle in which said ester is applied consists essentially of an aqueous solution having a pH within the range of 7-8.

4. The method in accordance with claim 1 wherein said derivative comprises the 3-phosphate disodium salt of 17 beta-Estradiol.

5. The method in accordance with claim 4 wherein said steroid is dissolved in a vehicle consisting essentially of the composition of the human tear.

6. The method in accordance with claim 4 wherein said steroid or derivative is dissolved in a vehicle consisting essentially of the following components, of which the amounts are indicated in percentages by volume:

| | |
|---|---|
| Povidone USP | 1.67% |
| Hydroxy Ethylcellulose USP | 0.44% |
| Sodium Chloride USP | 0.6% |
| Dried Sodium Phosphate (Na$_2$HPO$_4$) USP | .3% |
| Disodium Edetate USP | .1% |
| Thimerosal USP | 0.004% |
| pH adjusted to 7 with dilute, HCl or NaOH | qs |
| Purified Water USP | qs |

7. The method in accordance with claim 6 in which said sex steroid has a concentration in said vehicle within the range 7 to 8 of percentages by volume.

* * * * *